United States Patent [19]

Michalos

[11] Patent Number: 5,556,403
[45] Date of Patent: Sep. 17, 1996

[54] SURGICAL NEEDLE HOLDER FOR SECURING A NEEDLE AT A SELECTED POSITION

[76] Inventor: Peter Michalos, 137 Hampton Rd., South Hampton, N.Y. 11968

[21] Appl. No.: 385,718

[22] Filed: Feb. 8, 1995

[51] Int. Cl.⁶ .................................................. A61B 17/00
[52] U.S. Cl. ...................... 606/148; 606/147; 606/205; 606/207
[58] Field of Search ................................. 606/139, 144, 606/145, 147, 148, 151, 205–208; 112/169, 80.03; 81/300, 318, 418, 426, 424.5, 426.5; 433/159

[56] References Cited

U.S. PATENT DOCUMENTS

| 668,911 | 2/1901 | Ermold | 606/147 |
|---|---|---|---|
| 888,710 | 5/1908 | Janeway | 81/426 |
| 1,876,792 | 9/1932 | Thompson | 606/147 |
| 2,397,823 | 4/1946 | Walter | 606/207 |
| 5,011,491 | 4/1991 | Boenko et al. | 606/207 |
| 5,100,421 | 3/1992 | Christoudias | 606/147 |
| 5,147,373 | 9/1992 | Ferzli | 606/148 |
| 5,417,701 | 5/1995 | Holmes | 606/147 |

FOREIGN PATENT DOCUMENTS 320767  12/1902  France ................................. 606/144

OTHER PUBLICATIONS

Edgerton, Milton T., "The Art of Surgical Technique," pp. 130–133; 1988; Williams & Wilkins, Baltimore, MD.
Storz Ophthalmic Instruments catalog, pp. 71, 81, andd 82; 1988; Storz Instrument Company, St. Louis, Mo.

Primary Examiner—Michael Powell Buiz
Assistant Examiner—Jeffrey A. Schmidt
Attorney, Agent, or Firm—Jerome D. Jackson

[57] ABSTRACT

A surgical needle holder for facilitating safe and efficient surgery. The surgical needle holder has a plurality of grooves to secure a surgical needle at a selected position within the holder.

3 Claims, 19 Drawing Sheets

SURGICAL NEEDLE HOLDER FOR SECURING A NEEDLE AT A SELECTED POSITION

BACKGROUND OF THE INVENTION

1. Field of the Invention

This invention relates generally to surgical needle holders, and, more particularly, to a needle holder for facilitating safe and efficient surgery.

2. Description of Related Art

A typical surgical procedure employs a needle holder to allow the surgeon to manipulate surgical needles and suture. A needle can assume various positions within the needle holder. In some surgical maneuvers, the needle should consistently be in a certain position each time the surgeon passes the needle through the tissue being sutured. Adjusting a needle within a conventional needle holder, to ensure that the needle is in a certain position, can be an awkward and error prone task. Furthermore, adjusting the needle by hand after the needle has penetrated the patient's tissue carries the risk of disease transmission.

SUMMARY OF THE INVENTION

It is an object of the present invention to provide a surgical needle holder for efficiently manipulating a surgical needle.

To achieve this and other objects of the present invention, a surgical needle holder comprises a first member including a first handle and a first jaw coupled to the first handle, the first jaw defining a first flat surface; and a second member, pivotally coupled to the first member to allow movement of the needle holder between an open position and a closed position, the second member including a second handle and a second jaw coupled to the second handle, the second jaw defining a longitudinal axis, a second flat surface defining a length along the longitudinal axis, the second flat surface being opposed to the first flat surface when the needle holder is in the closed position, a third flat surface defining a length along the longitudinal axis, the third flat surface being opposed to the first flat surface when the needle holder is in the closed position, and a groove between the second and third flat surfaces, the groove being oriented transverse to the longitudinal axis, the groove having a first rim delineating the second flat surface, and a second rim delineating the third flat surface, the length of the second flat surface being greater than a distance between the first and second rims, the length of the third flat surface being greater than the distance between the first and second rims.

According to another aspect of the invention, a surgical needle holder comprises a first member including a first handle and a first jaw coupled to the first handle, the first jaw defining a first flat surface; and a second member, pivotally coupled to the first member to allow movement of the needle holder between an open position and a closed position, including a second handle and a second jaw coupled to the second handle, the second jaw defining a longitudinal axis, and a plurality of grooves each defining a groove width, each groove oriented transverse to the longitudinal axis, wherein each groove width is less than a distance between adjacent grooves.

According to yet another aspect of the present invention, in an operating theater a needle, surgical suture coupled to the needle, the surgical needle holder discussed in the previous paragraph, and a wound, the wound including subcutaneous tissue, a first tissue part, and a second tissue part, a method of using the surgical needle holder, the method comprising the step of: grasping the needle in a selected one of the plurality of grooves using the surgical needle holder, and the subsequent steps, performed a plurality of times without a direct manual adjustment of the needle within the surgical needle holder, of: subsequently driving the needle through the first and second tissue parts using the surgical needle holder; releasing the needle; regrasping the needle in the selected one of the plurality of grooves; and pulling the needle free of the first skin part.

The accompanying drawings which are incorporated in and which constitute a part of this specification, illustrate embodiments of the invention and, together with the description, explain the principles of the invention, and additional advantages thereof.

DESCRIPTION OF THE PREFERRED EMBODIMENTS

Figure 1:
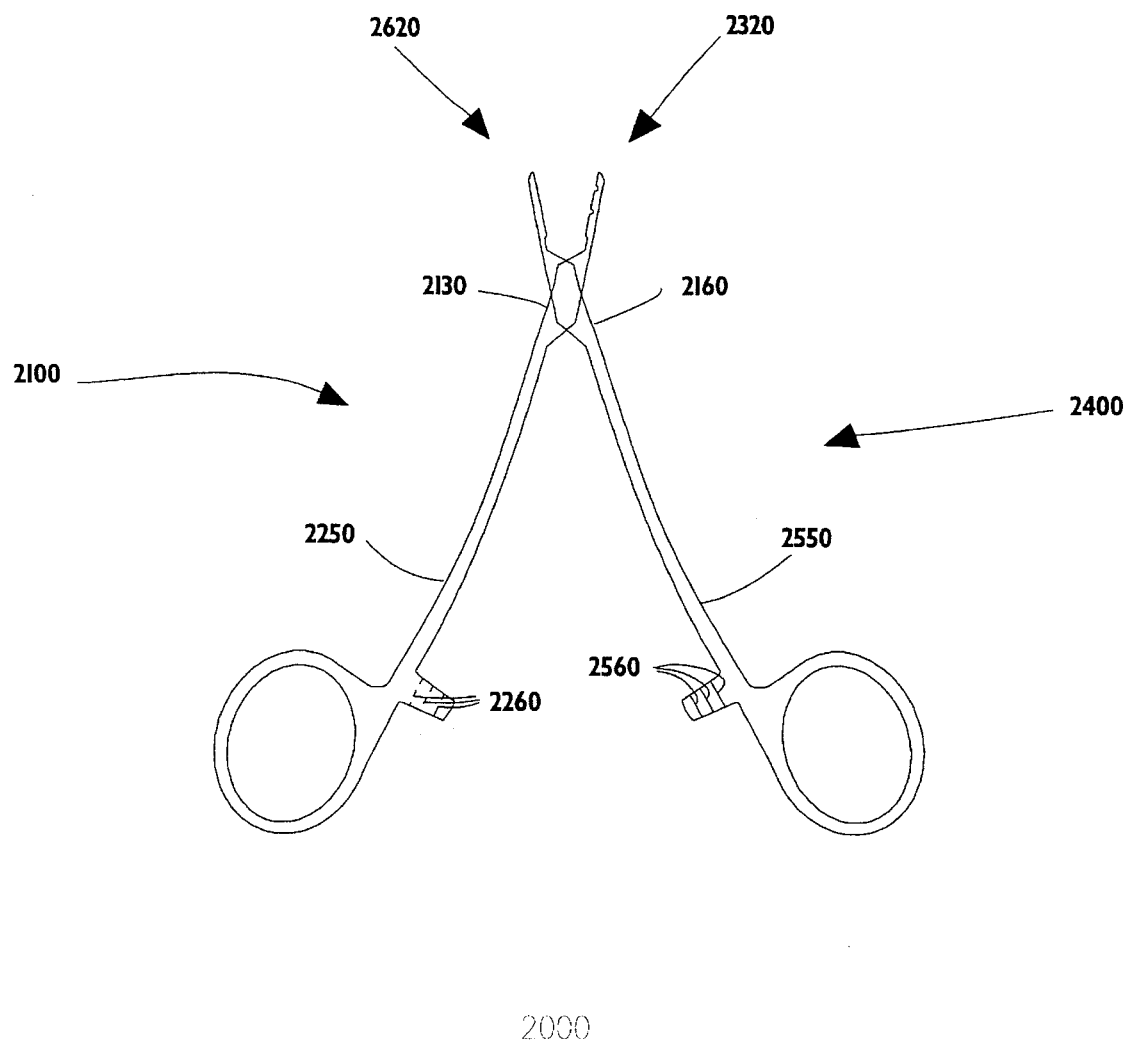
FIG. 1 is a front view of a surgical needle holder in the open position according to a first preferred embodiment of the present invention.

FIG. 1 shows needle holder 2000 according to a first preferred embodiment of the present invention. Needle holder 2000 has two halves: a left member 2100 and a right member 2400. Left member 2100 includes a handle 2250, a middle portion 2130, and a jaw 2320. Jaw 2320 has a plurality of continuously flat, smooth surfaces and a plurality of grooves, as discussed in more detail below. Right member 2400 includes a handle 2550, a middle portion 1160 pivotally coupled to middle portion 2130, and a jaw 2620. Jaw 2620 has a single continuously flat, smooth surface.

Right member 2400 includes ratchet teeth 2560, projecting out of the plane of the page of FIG. 1. Left member 2100 includes ratchet teeth 2260 (not directly visible in FIG. 1). When needle holder 2000 is in the closed position, ratchet teeth 2560 mate with ratchet teeth 2260. Thus, ratchet teeth 2560 and 2260 together constitute a locking mechanism for securing needle holder 2000 in the closed position.

Figure 2:
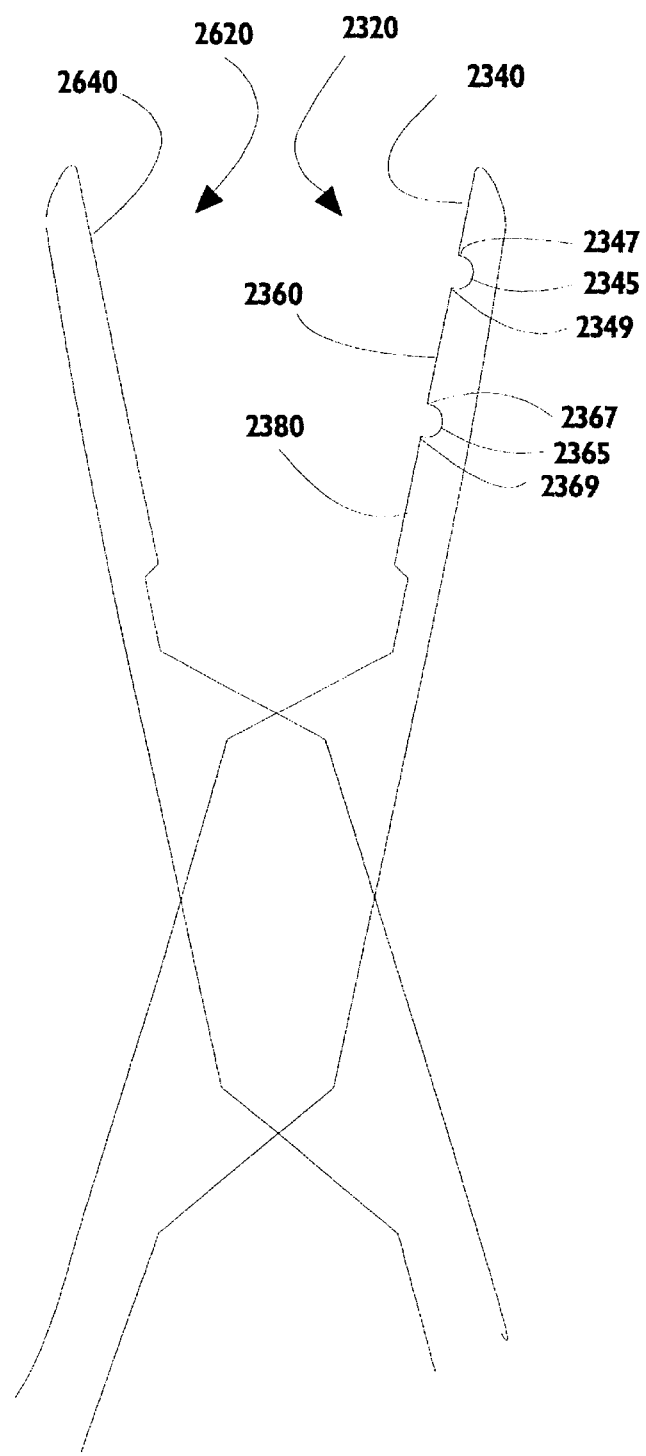
FIG. 2 is an enlarged view of a portion of the needle holder shown in FIG. 1
Figure 3:
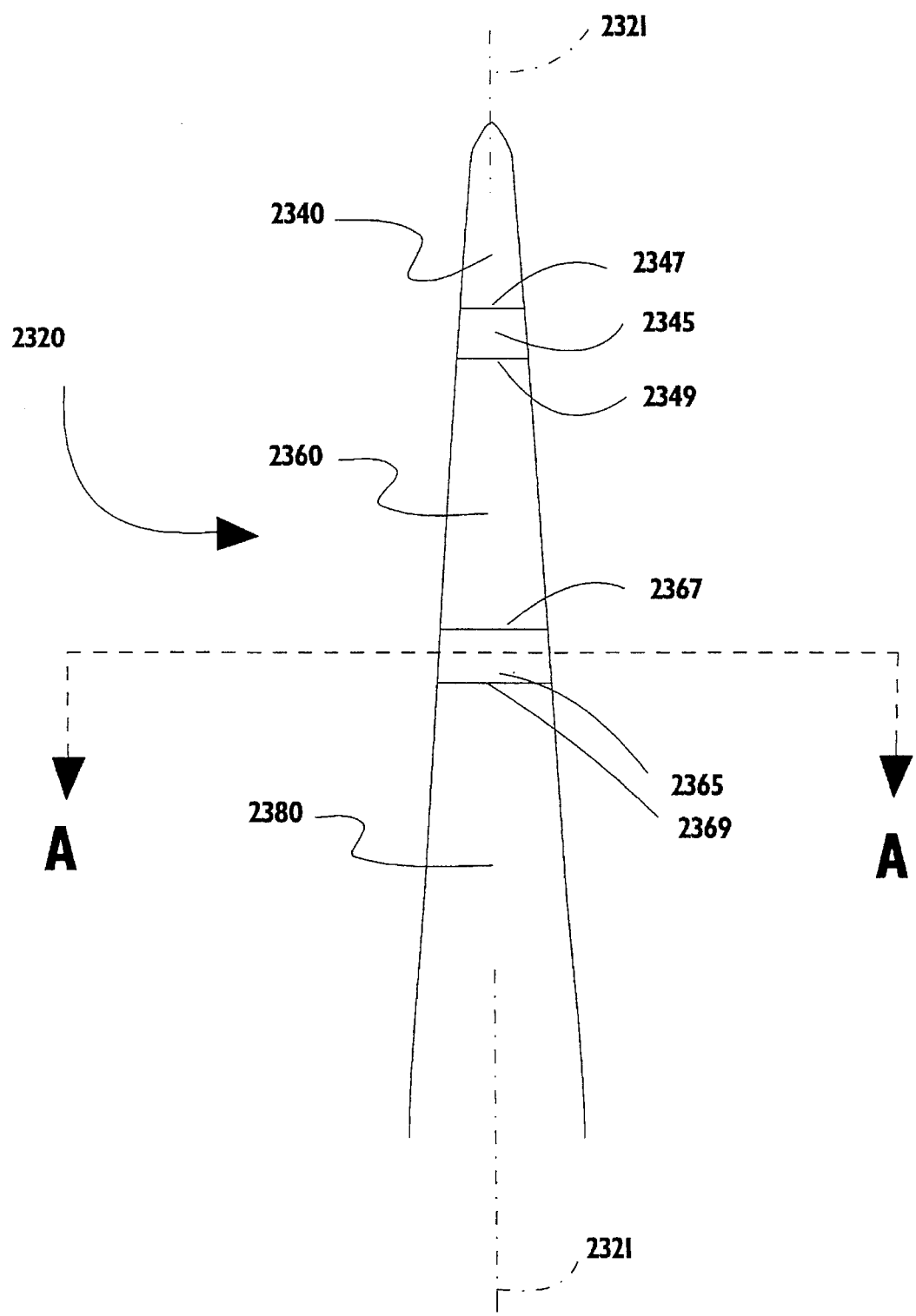
FIG. 3 is a side view of a portion of the needle holder shown in FIG. 2.

FIG. 2 shows an enlarged view of a portion jaws 2620 and 2320 of the first preferred needle holder 2000, and FIG. 3 shows a further enlarged side view of jaw 2320. Jaw 2620 defines a continuously flat, smooth surface 2640. Jaw 2320 defines a continuously flat, smooth surface 2340, a continuously flat, smooth surface 2360, and a continuously flat, smooth surface 2380. Each of grooves 2345 and 2365 is oriented perpendicular to the longitudinal axis 2321 of jaw 2320. Groove 2345 has a rim 2349 extending across the width of jaw 2320 and a rim 2349 extending across the width of jaw 2320. Groove 2365 has a rim 2367 extending across the width of jaw 2320 and a rim 2369 extending across the width of jaw 2320.

Grooves 2345 and 2365 are not drawn to scale. Jaw 2320 is approximately 9 mm in length, while grooves 2345 and 2365 have a groove width of slightly less than 0.1 mm from rim to rim.

Figure 4:
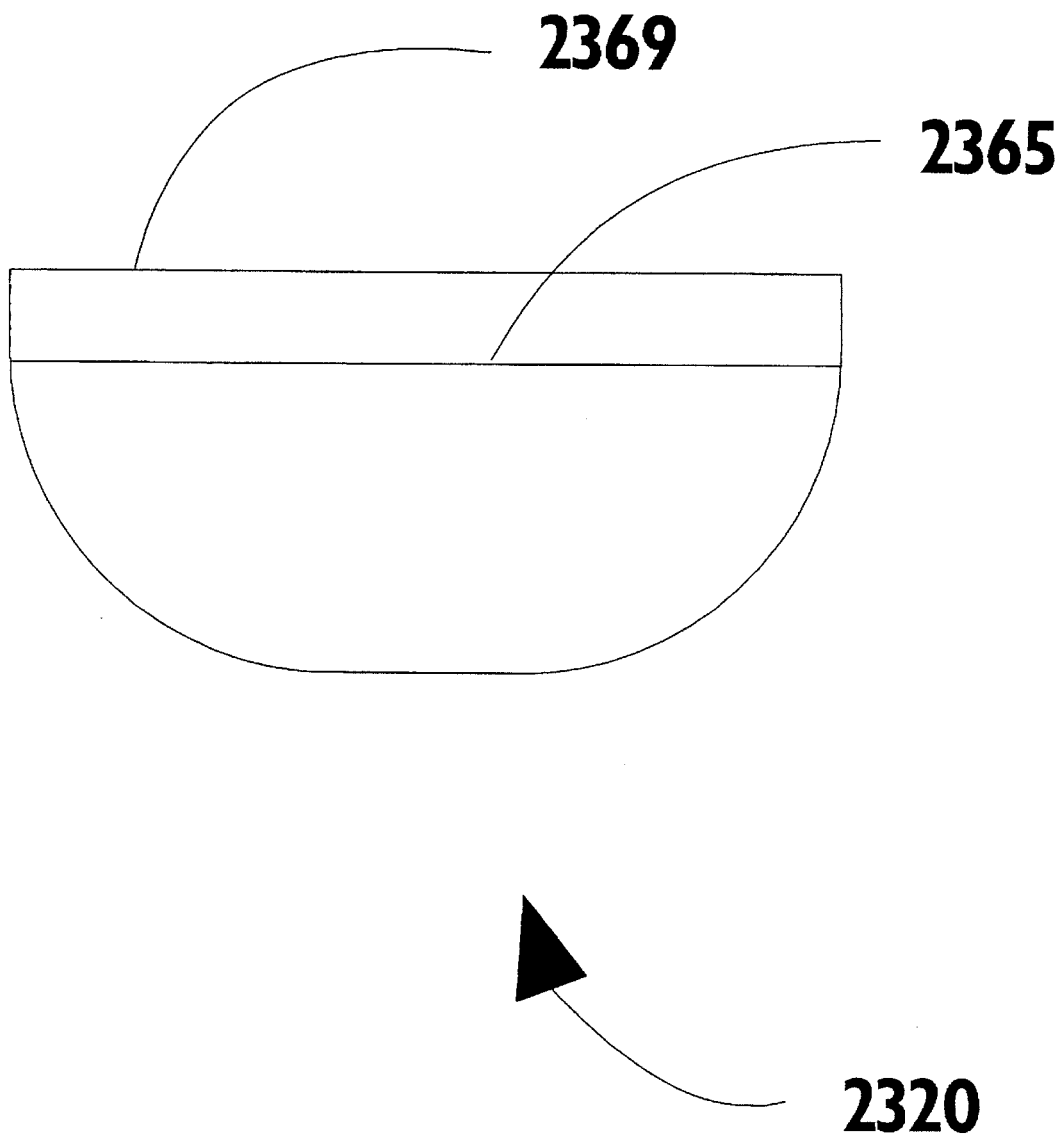
FIG. 4 is a cut-away view taken along the line A—A in FIG. 3.

FIG. 4 shows a cut-away view of jaw 2320, taken along the line A—A shown in FIG. 3.

Figure 5:
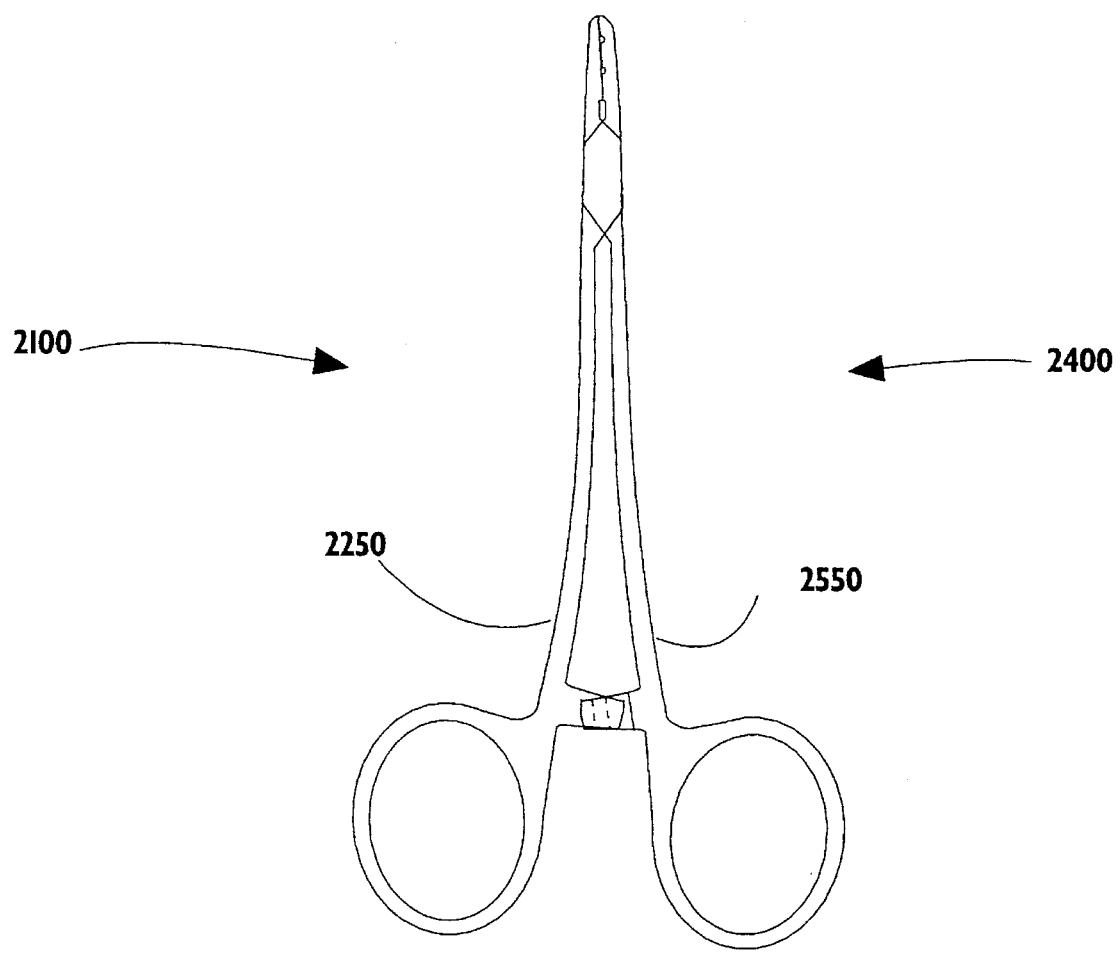
FIG. 5 is the front view of the first preferred needle holder in a closed position.

FIG. 5 shows needle holder 2000 in the closed position. In the closed position, needle holder 2000 is approximately 120 mm in length.

Figure 6:
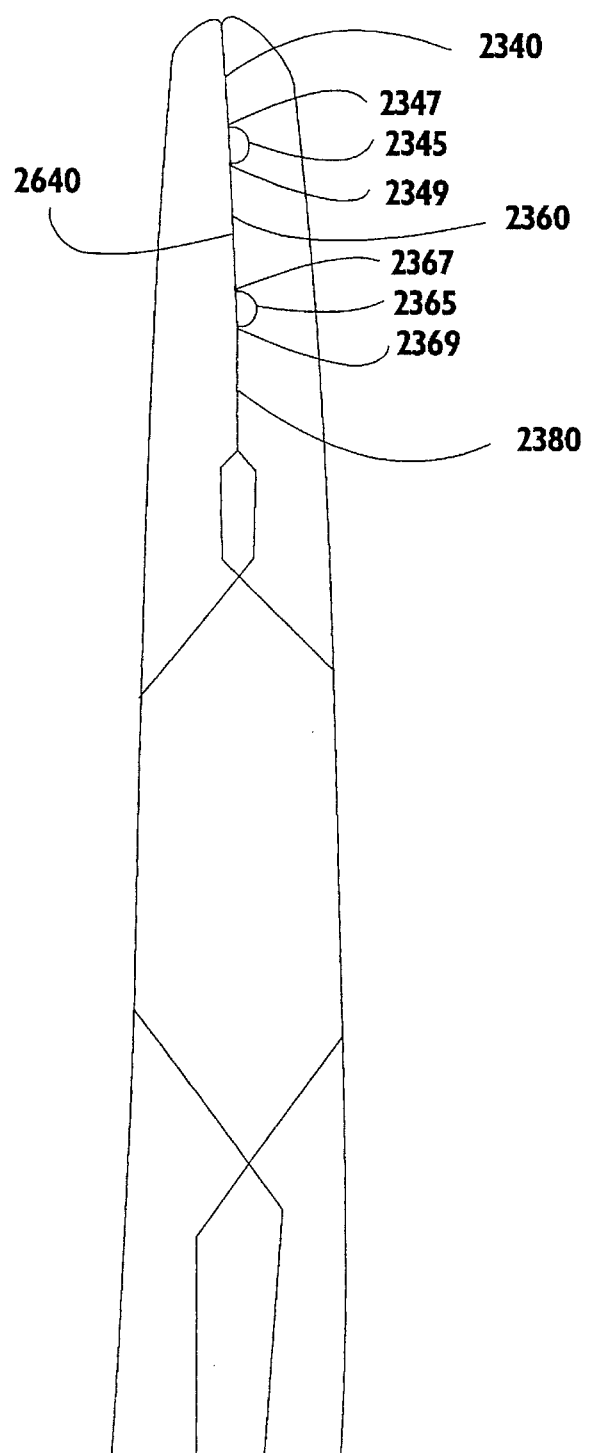
FIG. 6 is an enlarged view of a portion of the needle holder shown in FIG. 5.
Figure 7:
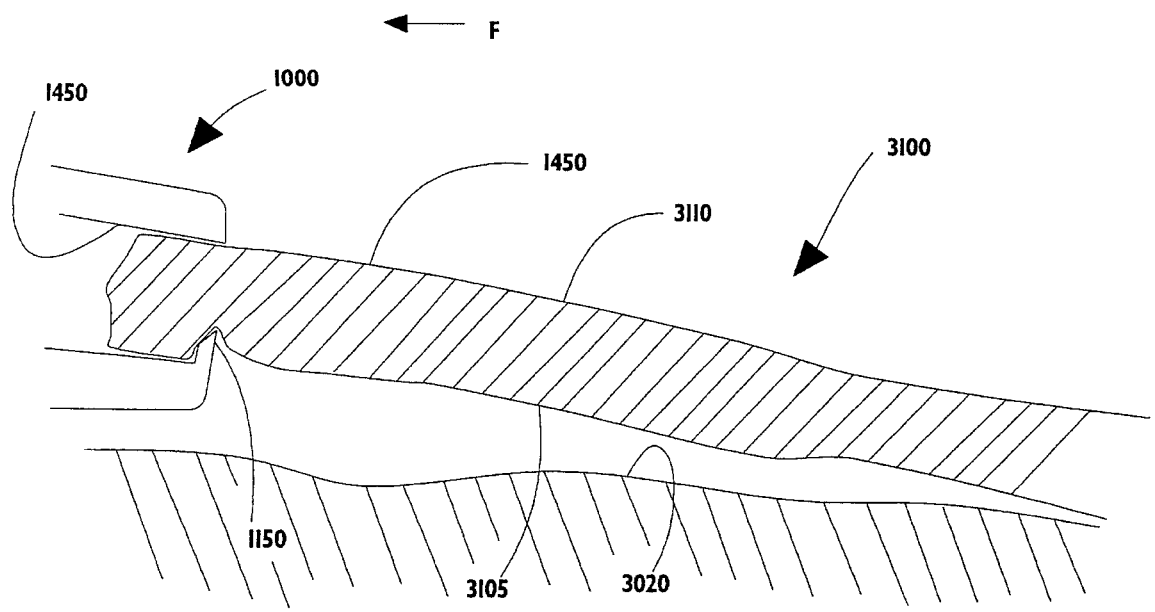
FIG. 7 is a cross-section view of a part of an operating procedure employing the first preferred needle holder.

FIG. 6 shows an enlarged view of a portion of the needle holder shown in FIG. 5. In FIG. 6, each of surfaces 2340, 2360, and 2380 is opposed to surface 2640.

Surgical needles may have a variety of diameters. A needle for abdominal surgery on humans may be 0.5 mm in diameter at the widest part of the needle. A needle for ophthalmic surgery may be 0.1 mm in diameter. The width of the grooves of needle holder 2000, from rim to rim, corresponds to the diameter(s) of the surgical needles that needle holder 2000 is to hold. The width of groove 2345 can be somewhat less than the diameter of the needle being held and still secure the needle. The width of groove 2345 should not be greater than the diameter of the needle being held, however, because such a width would allow movement of a needle within groove 2345.

In other words, needle holder 2000 includes right member 2400 having handle 2550 and jaw 2620 coupled to handle 2550, through middle portion 2160, jaw 2620 defining surface 2640. Needle holder 2000 also includes left member 2100, pivotally coupled to right member 2400 to allow movement of the needle holder between an open position and a closed position, left member 2100 including handle 2250 and jaw 2320 coupled to handle 2250, jaw 2320 defining a longitudinal axis 2321, surface 2380 defining a length along the longitudinal axis, surface 2380 being opposed to surface 2640 when the needle holder is in the closed position, surface 2360 defining a length along axis 2321, surface 2360 being opposed to surface 2640 when the needle holder is in the closed position, and a groove 2365 between surfaces 2380 and 2360, groove 2365 being oriented transverse to axis 2321, groove 2365 having rim 2369 delineating surface 2380, and rim 2367 delineating surface 2360, the length of surface 2380 being greater than a distance between rims 2367 and 2369, the length of surface 2360 being greater than the distance between rims 2367 and 2369. Jaw 2320 also includes surface 2340 defining a length along axis 2321, surface 2340 being opposed to surface 2640 when the needle holder is in the closed position, and groove 2345 between surfaces 2360 and 2340, groove 2345 being oriented transverse to axis 2321, groove 2345 having a rim 2349 delineating surface 2360, and a rim 2347 delineating surface 2340, the length of surface 2340 being greater than a distance between rims 2347 and 2349.

In general, the surgeon informs the scrub nurse of the surgeon's choice of needle, suture size, and needle position with the needle holder. For example the surgeon may indicate 6-0 nylon suture, and "outer position." The scrub nurse would then open a 6-0 needle packet, place a 6-0 needle into groove 2345, thread nylon suture through the suture hole of the needle, engage the ratchet lock to lock the needle holder in the closed position, and hand the loaded needle holder to the surgeon on the surgeon's request. The surgeon then drives the needle through tissue, inscribing a small half-circle that matches the curve of the needle. As the needle exits the tissue, the surgeon grasps the exiting part of the needle with holder 2000. The exiting needle is grasped into groove 2345.

If the surgeon instead indicates "inner position" the scrub nurse would place the needle into groove 2365. The surgeon would then drive the needle through tissue and, as the needle exits the tissue, the surgeon would grasp the exiting part of the needle into groove 2365 of holder 2000.

The loaded needle holder constitutes a surgical assembly comprising needle holder 2000; needle 5000, which defines a suture hole, needle 5000 being located in one of the grooves of needle holder 2000; and surgical suture in the suture hole.

FIGS. 7 through 14 show a preferred method for suturing two opposing wound edges using needle holder 2000. As shown in cross-section in FIG. 7, first skin part 3100 is dermal tissue above subcutaneous tissue 3020. Subcutaneous tissue 3020 may be fat or muscle. The surgeon grasps first skin part 3100 with teeth 1150 of forceps 1000 grasping the subcutaneous (inside) surface 3105 of first skin part 3100, and smooth part 1450 of forceps 1000 grasping the epidermal (outside) surface 3110. The surgeon then pulls first skin part 3100 in the direction of arrow F shown in FIG. 7 and everts first skin part 3100 by rolling first skin part 3100 away from subcutaneous tissue 3020 as shown in cross-section in FIG. 8.

Forceps 1000 are specially configured to allow efficient manipulation of tissue while avoiding certain types of damage to external tissue, as described in detail in copending U.S. PATENT APPLICATION of PETER MICHALOS for SURGICAL FORCEPS, filed concurrently with the instant application on Feb. 8, 1995. The contents of this copending application is herein incorporated by reference.

Figure 8:
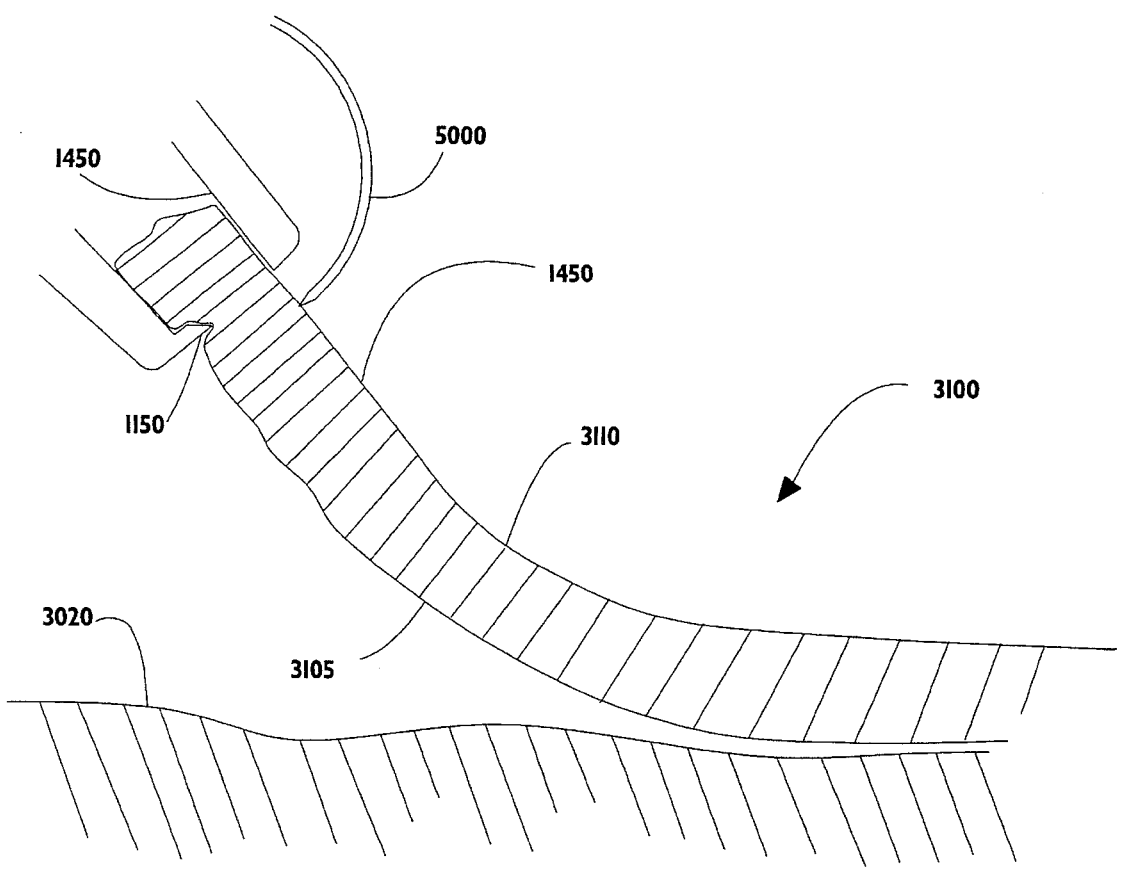
FIG. 8 is a cross-section view of another part of the operating procedure.
Figure 10:
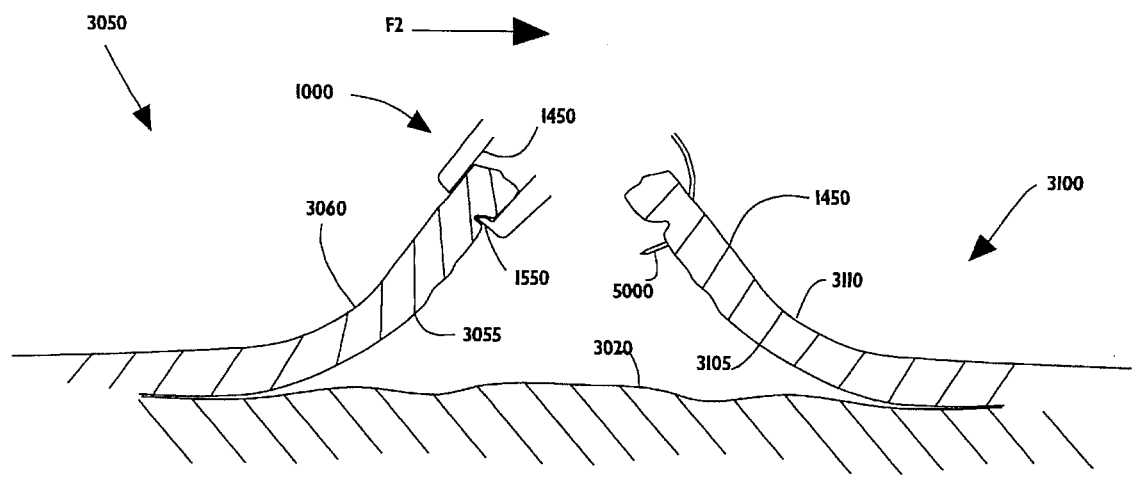
FIG. 10 is a cross-section view of yet another part of the operating procedure.
Figure 9:
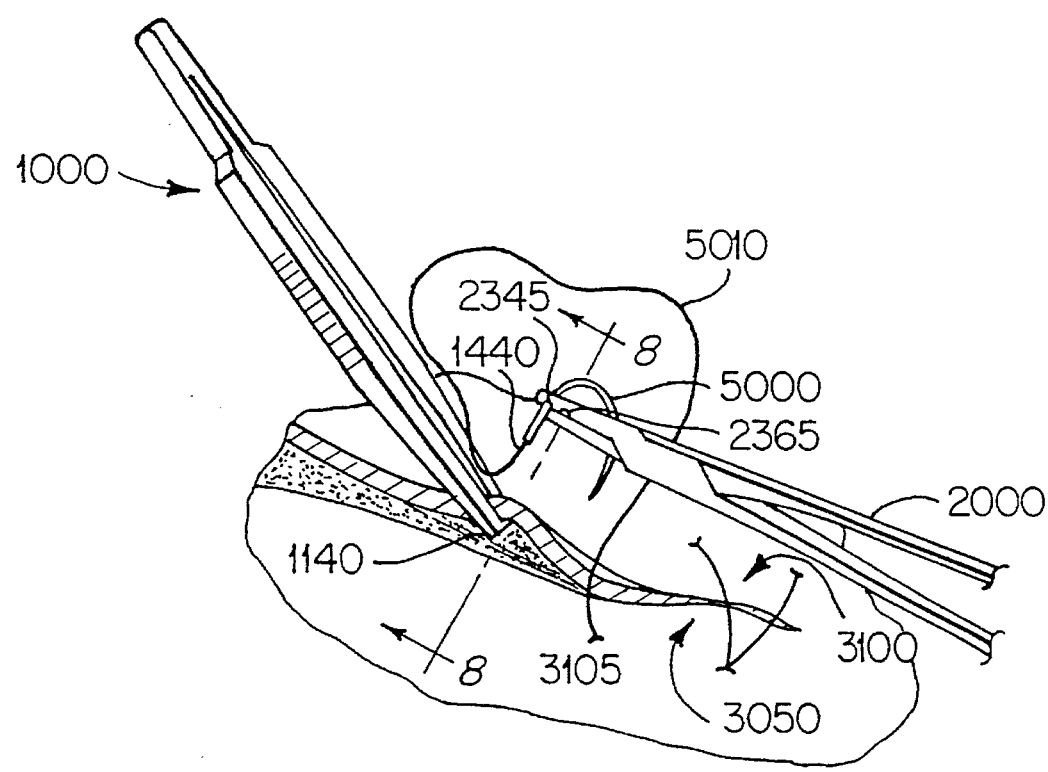
FIG. 9 is a perspective view of the part of the operating procedure shown in FIG. 8.

FIG. 9 is a perspective view of the part of the procedure shown in FIG. 8; FIG. 8 is a side view taken along the line B—B shown in FIG. 9. As shown in FIGS. 8 and 9, the pulling action reapproximates first skin part 3100 with second skin part 3050, meaning that the pulling action aligns first skin part 3100 with second skin part 3050. The surgeon uses needle holder 2000 to grasp needle 5000 into groove 2345 at an initial position along needle 5000, at the back part of the shaft, and presses the tip of needle 5000 straight downward. The eversion of first skin part 3100 by forceps 1000 allows the surgeon to view needle 5000 as needle 5000 emerges from the subcutaneous surface 3105 of first skin part 3100.

After needle 5000 emerges from subcutaneous surface 3105, the surgeon ceases to grip first skin part 3100 with forceps 1000. The surgeon then grasps second skin part 3050 with teeth 1150 grasping the subcutaneous (inside) surface 3055 of second skin part 3050, and smooth part 1450 grasping the epidermal (outside) surface 3060. The surgeon then pulls second skin part 3050 in the direction of arrow F2 shown in cross-section in FIG. 10 and everts second skin part 3050 by rolling second skin part 3050 away from subcutaneous tissue 3020. The pulling action reapproximates second skin part 3050 with first skin part 3100. The eversion of second skin part 3050 by forceps 1000 allows the surgeon to view the tip of needle 5000 as it penetrates subcutaneous surface 3055. Grasping second skin part 3050 also produces a counter pressure as needle 5000 penetrates the subcutaneous surface 3055 of second skin part 3050.

Figure 11:
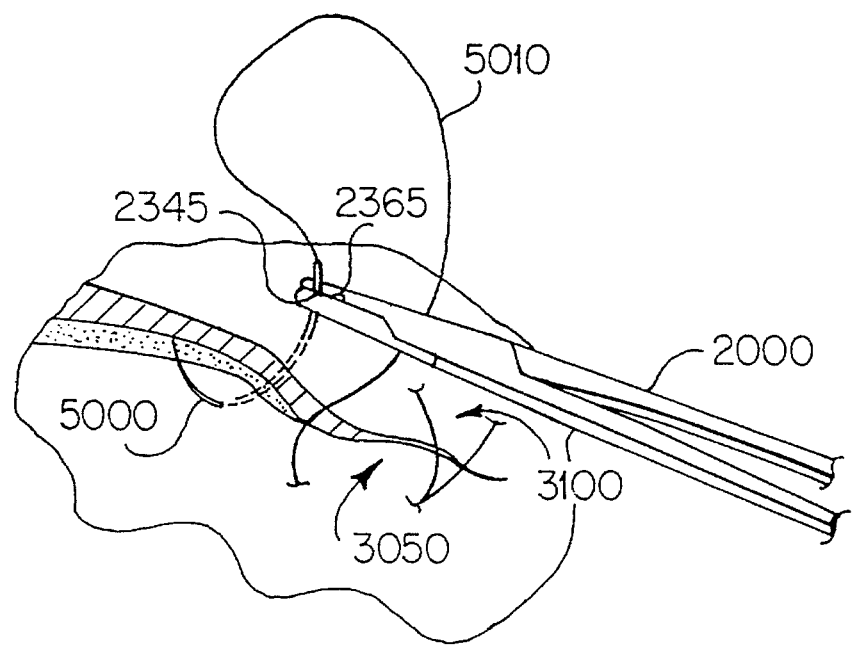
FIG. 11 is a perspective view of yet another part of the operating procedure.
Figure 12:
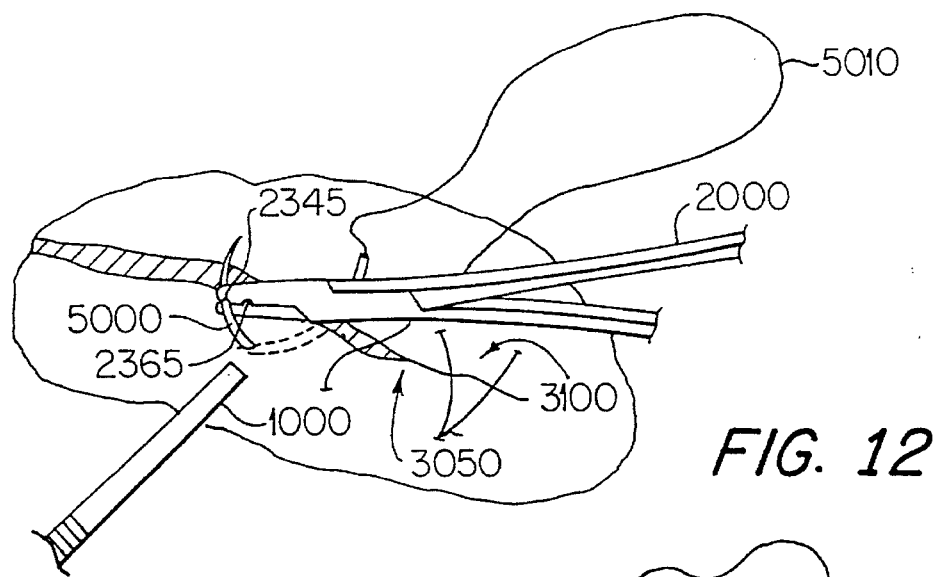
FIG. 12 is a perspective view of yet another part of the operating procedure.
Figure 13:
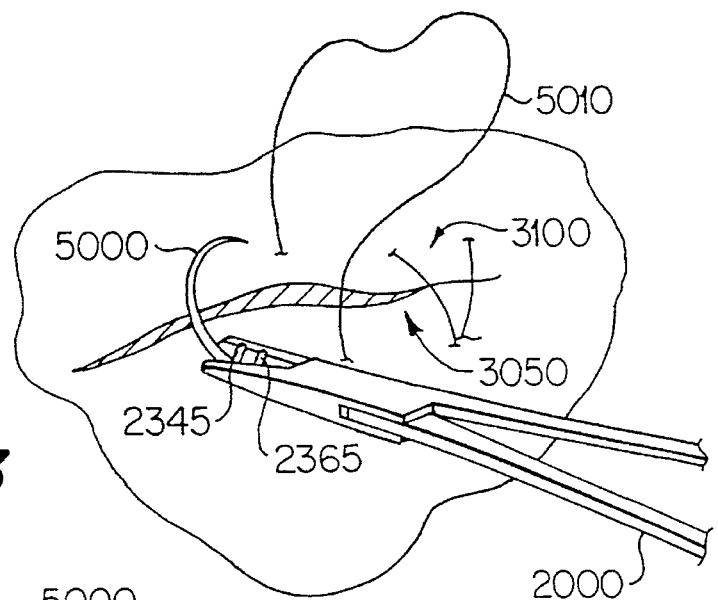
FIG. 13 is a perspective view of yet another part of the operating procedure.

Once the tip of needle 5000 emerges from epidermal surface 3060 of second skin part 3050 as shown in FIG. 11, the surgeon causes forceps 1000 to release second skin part 3050 and causes needle holder 2000 to release the back part of needle 5000. As shown in FIG. 12, the surgeon then causes needle holder 2000 to grasp the emerging part of needle 5000. The surgeon uses needle holder 2000 to pull needle 5000 partially out of second skin part 3050, while exerting a counterpressure with the but end of forceps 1000. Before needle 5000 is clear of second skin part 3050, the surgeon releases the jaws of needle holder 2000 and slides the jaws of needle holder 2000 down the shaft of needle 5000 to the initial position, near the back of the shaft of needle 5000, as shown in FIGS. 13 and 14.

Figure 14:
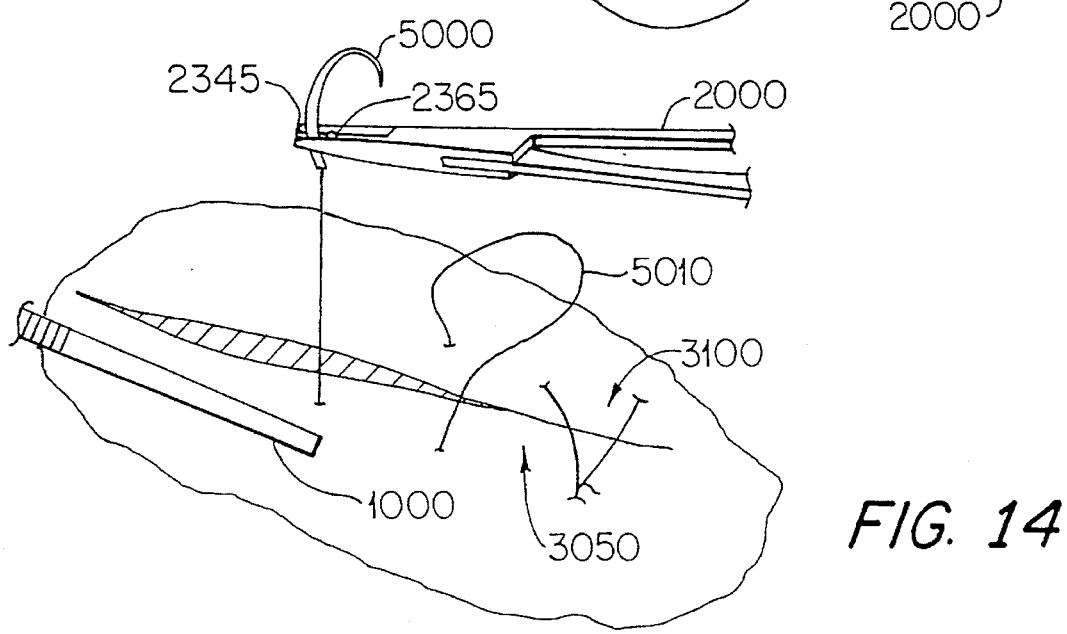
FIG. 14 is a perspective view of yet another part of the operating procedure.

The surgeon then causes needle holder 2000 to regrasp needle 5000 in groove 2345 and pull needle 5000 free of second skin part 3050, as shown in FIG. 14. As suture 4010 emerges, the surgeon exerts a counterforce with the but of forceps 1000. Her nondominant hand then grasps the suture, takes up the slack, and tightens the closure of the already sutured part of the wound. Because needle holder 2000 is now grasping needle 5000 in groove 2345 at the initial position along needle 5000, the surgeon may begin another stitch without repositioning needle 5000 within needle holder 2000.

Although the illustrated method places bites on both sides of the wound without an intervening release and regrasp of needle 5000, the surgeon may drive the needle into the first wound edge, release the needle, regrasp the needle at the part emerging from the first wound edge, and subsequently drive the needle through the second wound edge.

Although the illustrated method produces a running suture, a surgeon may make separately knotted stitches. More specifically, after the step shown in FIG. 14, instead of immediately beginning another stitch, the surgeon may cut the suture and place the loaded needle holder in a "neutral area," which is a platform where the surgeon may place and pickup instruments without the assistance of the scrub nurse. The surgeon then knots the recently completed stitch, picks up the loaded needle holder from the neutral area, and begins another stitch, as described in FIGS. 7 through 14.

In other words, the preferred method of using needle holder 2000 includes the step of grasping needle 5000 in a selected one of the plurality of grooves of needle holder 2000, the selected groove being groove 2345. The preferred method also includes the following subsequent steps, performed a plurality of times without a direct manual adjustment of needle 5000 within needle holder 2000: driving needle 5000 through the tissue parts 3100 and 3050 using the needle holder 2000; releasing needle 5000; regrasping needle 5000 in groove 2345; and pulling the needle free of the skin part 3050. In other words, the set of steps of driving, releasing, regrasping, and pulling is performed a plurality of times without a member of the surgical team touching the needle 5000 with her hands or gloves. Further, this set of steps is performed a plurality of times without touching needle 5000 with any instrument other than needle holder 2000.

Figure 15:
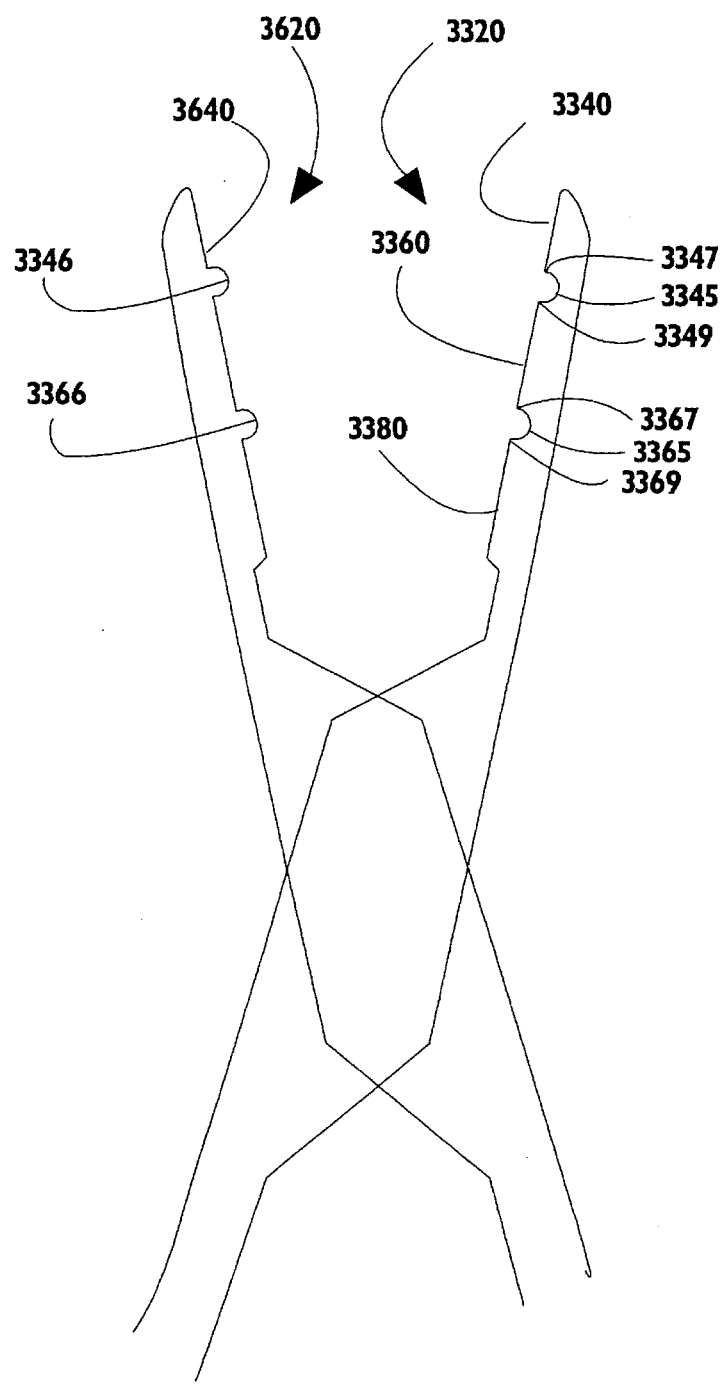
FIG. 15 is an enlarged front view of a needle holder in the open position in accordance with a second preferred embodiment of the present invention.

FIG. 15 shows an enlarged view of a portion of needle holder 3000 in the open position in accordance with a second preferred embodiment of the present invention. Jaw 3620 includes projections 3346 and 3366. Jaw 3320 includes grooves 3345 and 3365.

Figure 16:
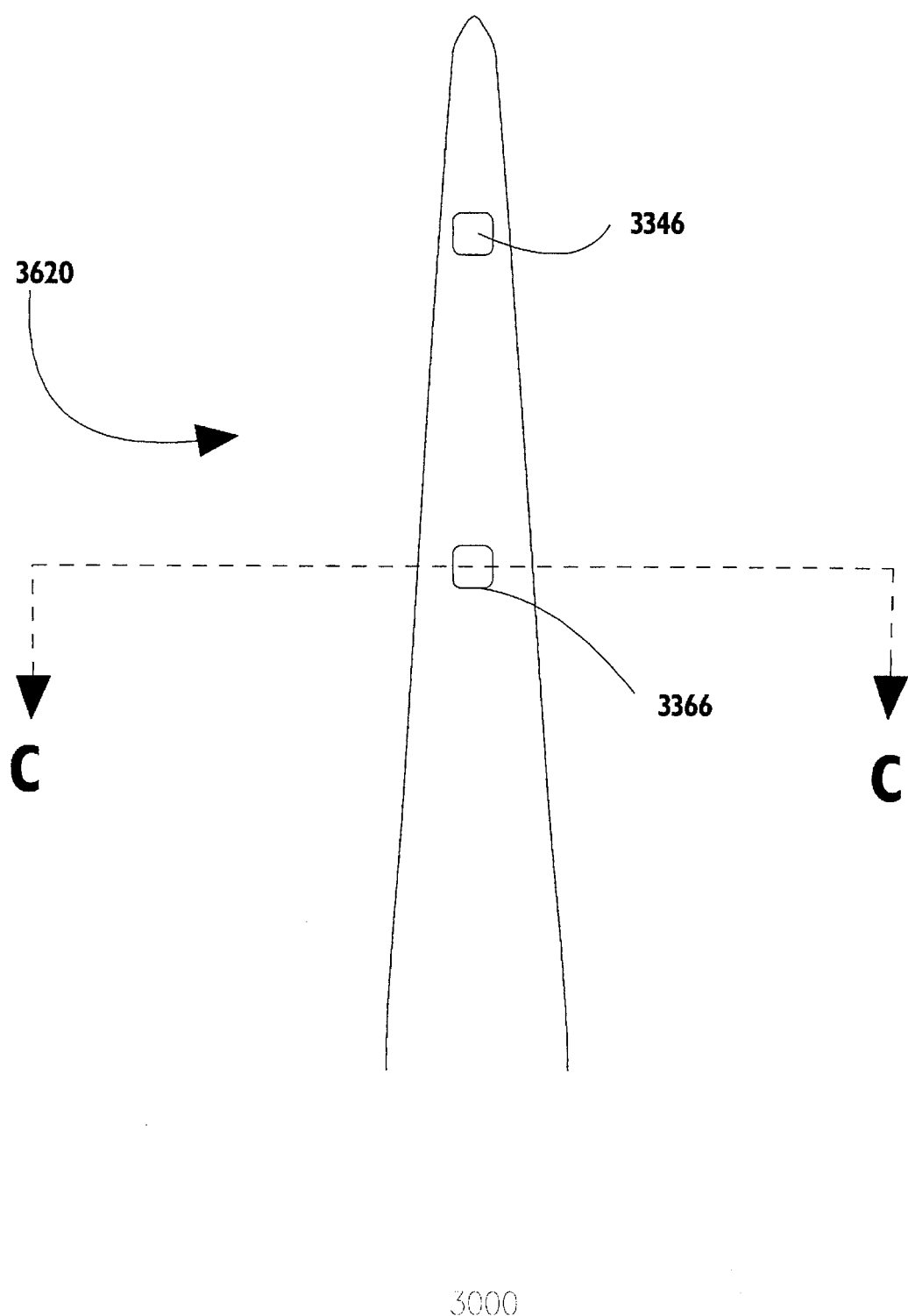
FIG. 16 is a side view of a portion of the needle holder shown in FIG. 15.
Figure 17:
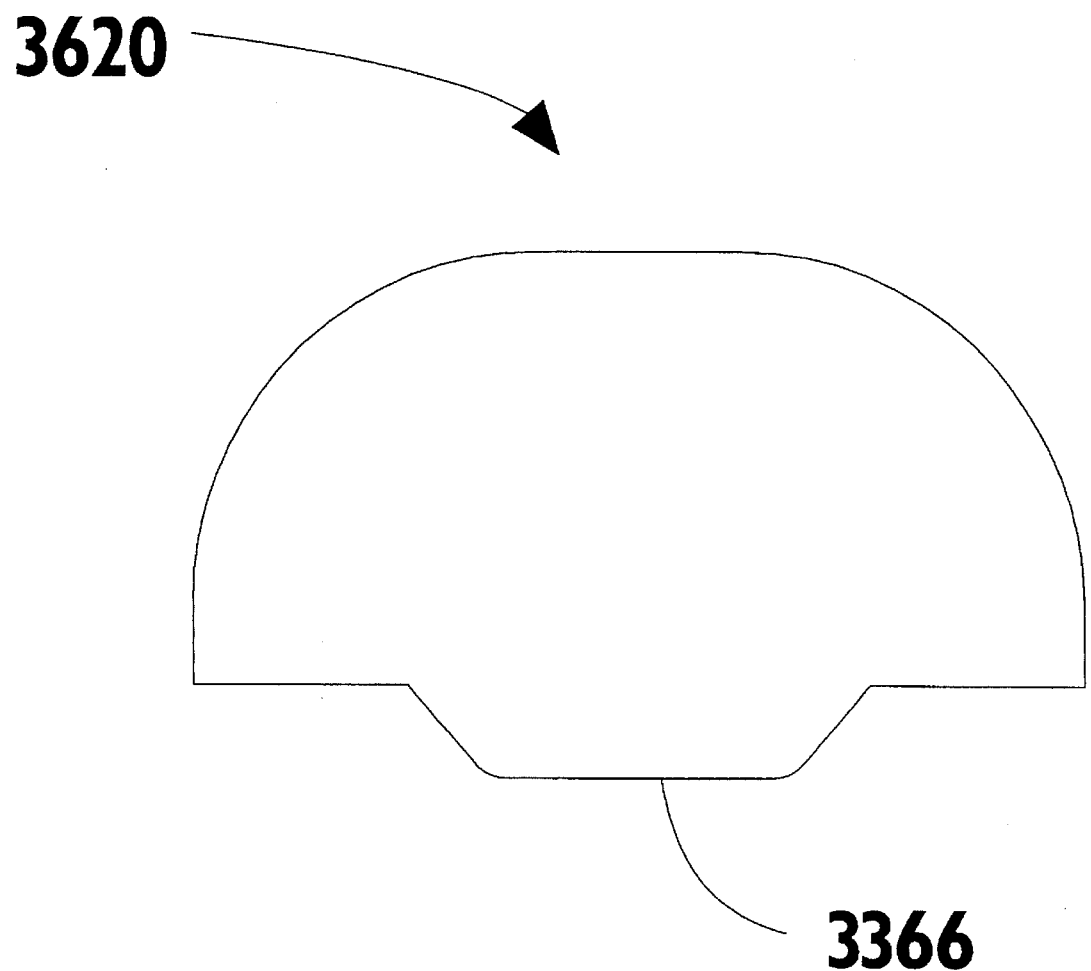
FIG. 17 is a cut-away view taken along the line C—C in FIG. 16.

FIG. 16 shows a side view of jaw 3620, and FIG. 17 shows a cut-away view of jaw 3620, taken along the line C—C shown in FIG. 16. Projection 3366 has a maximum height at the center of jaw 3620. In other words, projection 3366 has a maximum height removed from the edges of jaw 3620. Thus projection 3366 is shaped to accommodate an arc shaped needle. The height of projection 3366 is determined by the arcs of the needles that needle holder 3000 is to accommodate. Needles may have arcs corresponding to a radius of up to 0.5 cm for ophthalmic surgery, or may have arcs corresponding to a radius of up to 4 cm for other types of surgery.

Figure 18:
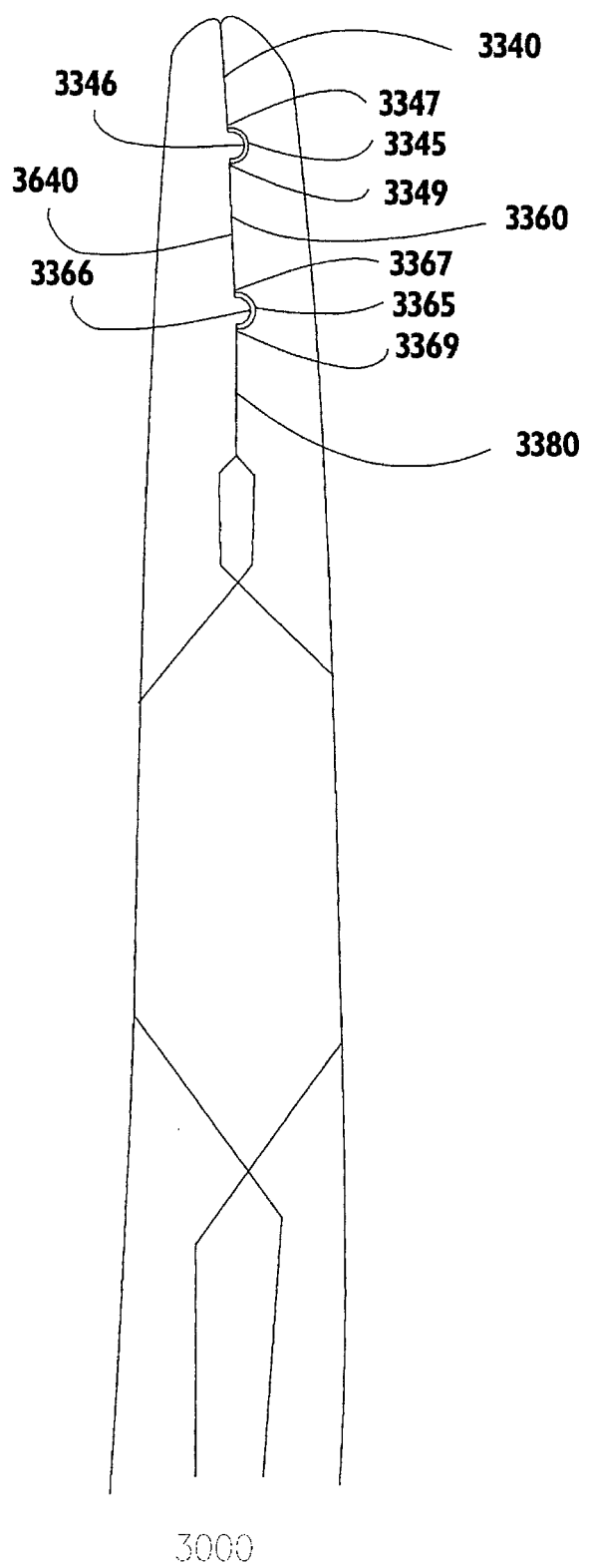
FIG. 18 is an enlarged front view of the second preferred needle holder in the closed position.

FIG. 18 shows needle holder 3000 in the closed position. Projection 3346 extends into groove 3345 and projection 3366 extends into groove 3365. The width of groove 3345 can be somewhat less than the diameter of the needle being held and still secure a needle. The width of groove 3345 can be greater than the diameter of the needle being held, because projection 3346 extends into groove 3345 to press the needle against the groove. Thus, projection 3346 allows needle holder 3000 to accommodate a greater range of needle diameters. Furthermore, because the grooves may in general be wider, needle holder 3000 is relatively easy to load.

Grooves 3345 and 3365 are not drawn to scale. Grooves 3345 and 3365 are 0.35 mm wide, from rim to rim, while jaw 3320 is 9 mm in length. Because the width of grooves 3345 and 3365 are 0.35 mm, needle holder 3000 is optimized for needle diameters in the range 0.1 to 0.3 mm.

Figure 19:
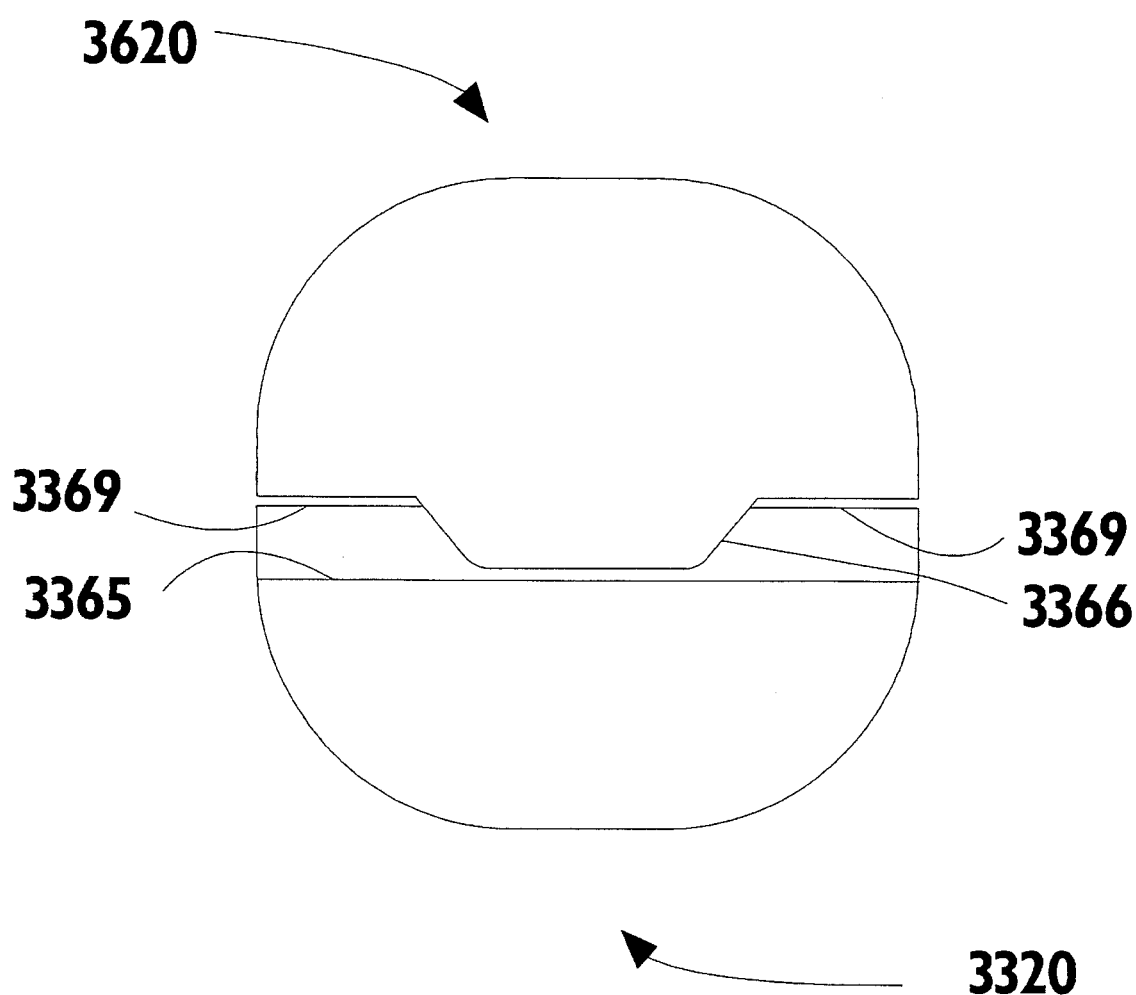
FIG. 19 is a cut-away view of the needle holder shown in FIG. 18.

FIG. 19 shows a cut-away view of groove 3365, including rim 3369 in jaw 3320, mated with projection 3366 in jaw 3620 when needle holder 3000 is in the closed position. The cut-away view of FIG. 19 is taken along the same position as that of the cut-away view of FIG. 17.

Other portions of second preferred needle holder 3000 are the same as corresponding portions of the first preferred needle holder 2000.

Figure 20:
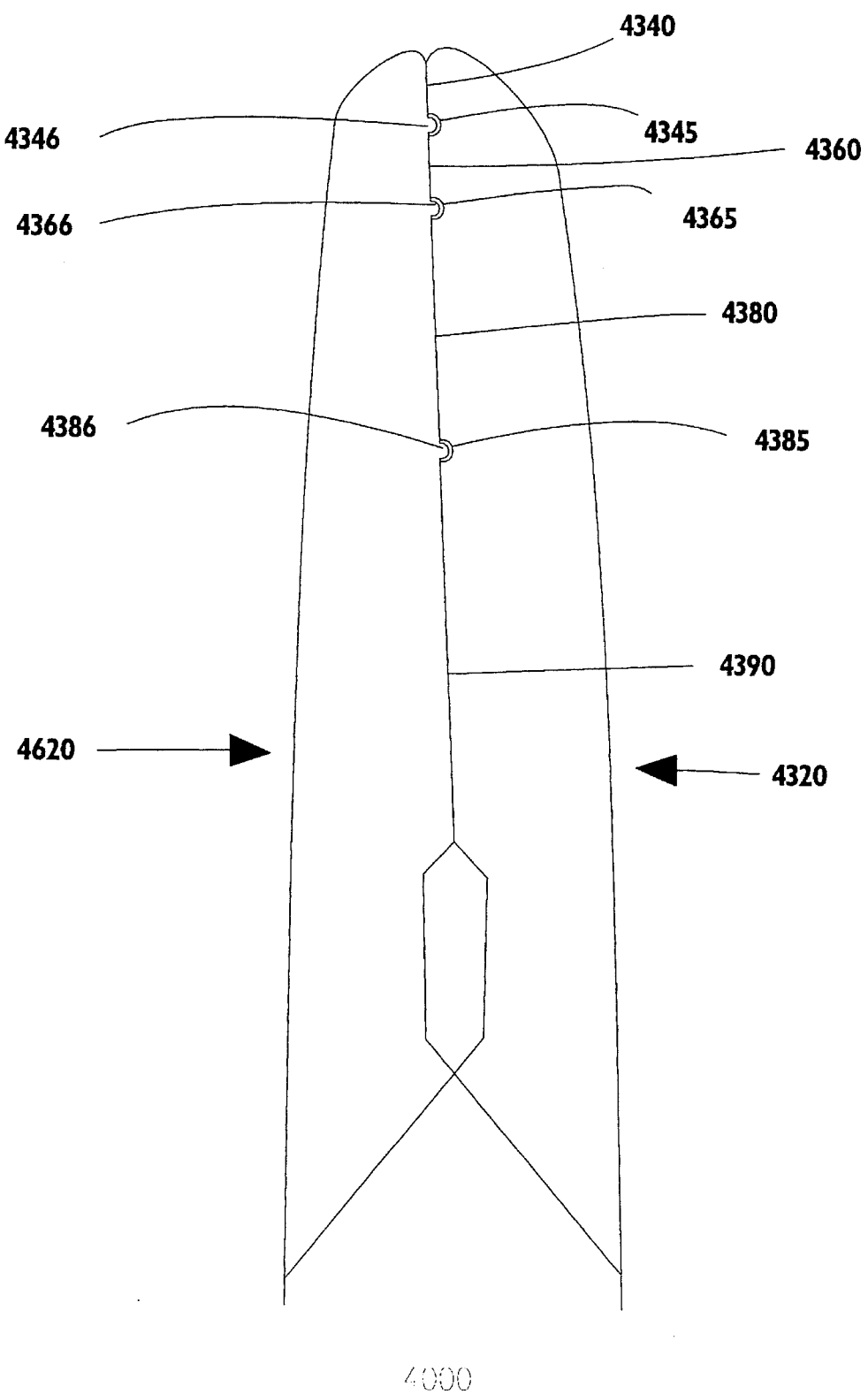
FIG. 20 is an enlarged front view of a needle holder in the closed position in accordance with a third preferred embodiment of the present invention.

FIG. 20 shows an enlarged view of a portion of needle holder 4000 in the closed position in accordance with a third preferred embodiment of the present invention. Jaws 4620 and 4230 are each 9 mm long. Preferred needle holder 4000 includes three grooves: a groove 4345 located 0.9 mm from the tip of jaw 4230, a groove 4365 located 1.8 mm from the tip of jaw 4230, and a groove 4385 located 4.5 mm from the tip of jaw 4345. Each of grooves 4345, 4365, and 4385 of jaw 4320 has a groove width of 0.35 mm. Surface 4340 of jaw 4320 has a length of 0.9 mm, surface 4360 of jaw 4320 has a length of 0.55 mm, surface 4380 of jaw 4320 has a length of 2.35 mm, and surface 4390 of jaw 4320 has a length of 4.15 mm. Thus, a ratio of a distance between grooves 4365 and 4385, to a groove width is greater than 5. In contrast, an insufficient distance between adjacent grooves increases the likelihood of accidentally causing the needle to straddle to grooves during loading, thereby damaging the needle.

Preferred needle holder 4000 also includes a projection 4346 opposing groove 4345, a projection 4366 opposing groove 4365, and a projection 4386 opposing groove 4385. Other portions of third preferred needle holder 4000 are the same as corresponding portions of the second preferred needle holder 3000.

Figure 21:
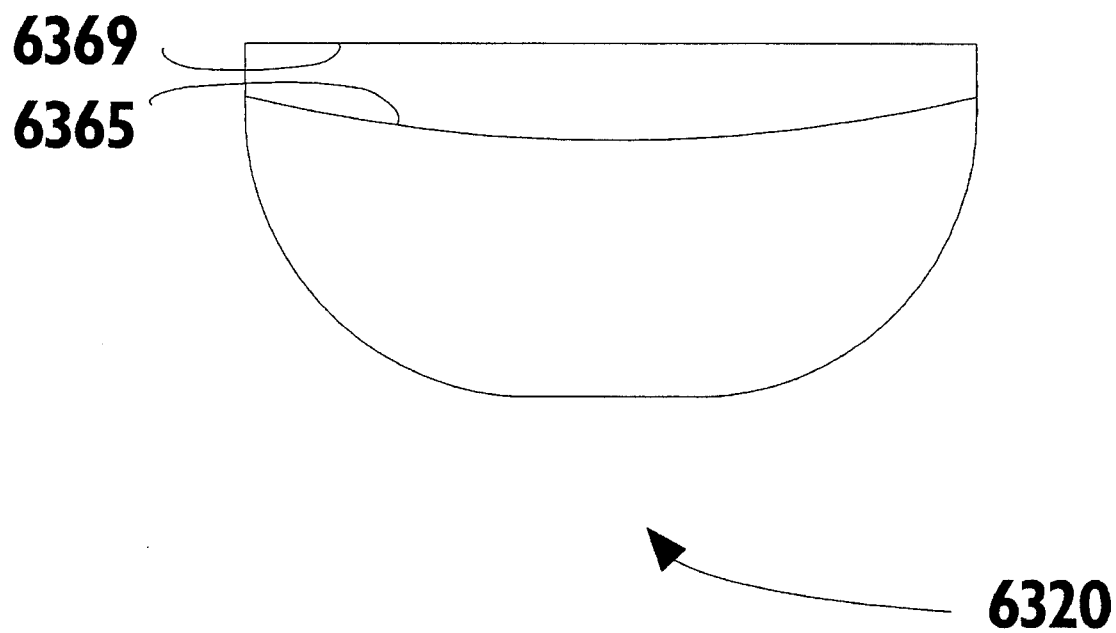
FIG. 21 is a cutaway view of a needle holder in accordance with a fourth embodiment of the present invention.
Figure 22:
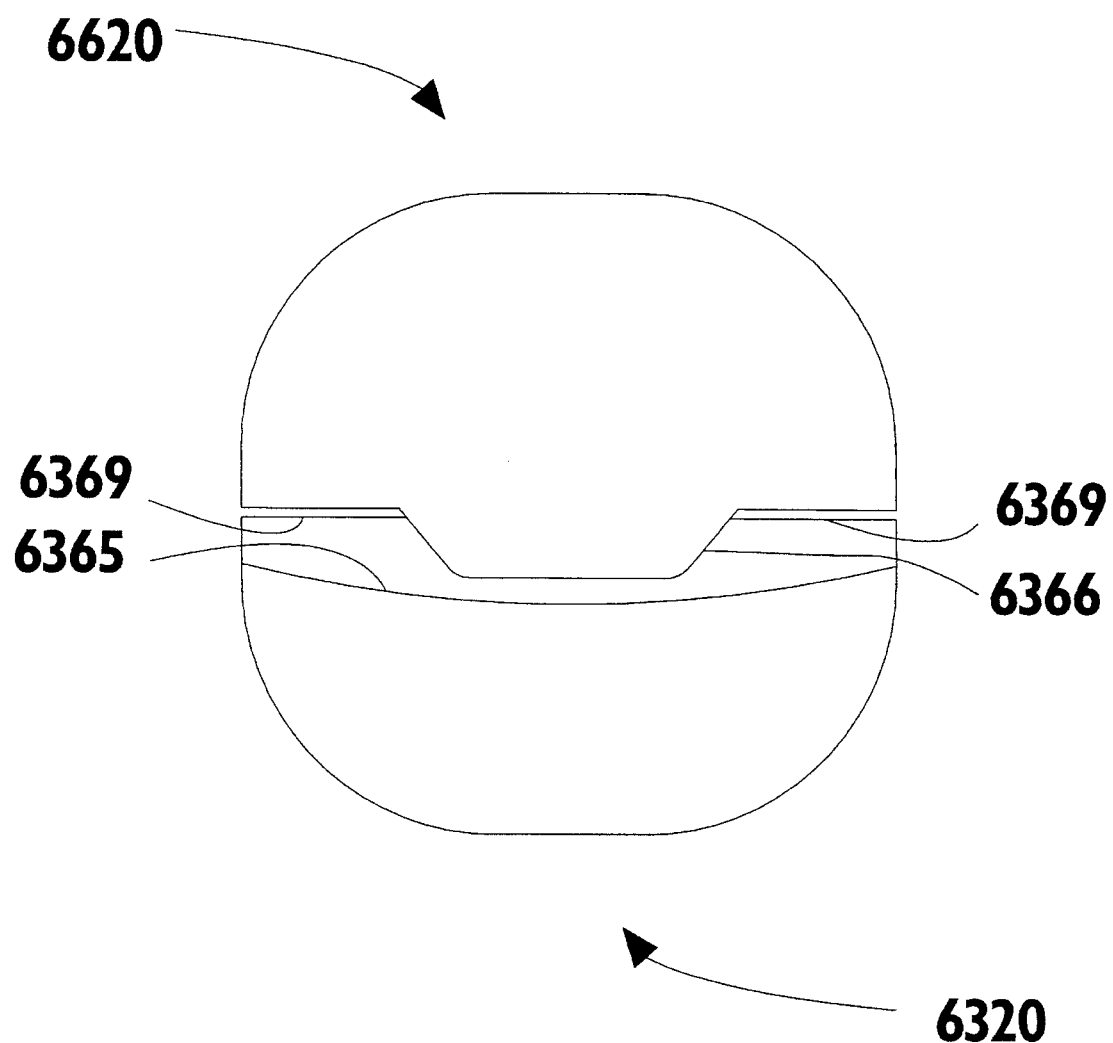
FIG. 22 is another cut-away view of the fourth preferred needle holder in the closed position.

FIGS. 21 and 22 show portions of needle holder 6000 in accordance with a fourth embodiment of the present invention. FIG. 21 shows a cut-away view of groove 6365 of needle holder 6000. The view of FIG. 21 showing needle holder 6000 is analogous to the cut-away view of FIG. 19 showing needle holder 3000. Groove 6365 in jaw 6320 is arc-shaped to accommodate an arc shaped needle. This arc corresponds to a radius of less than 1 cm, to accommodate ophthalmic surgical needles. Groove 6365 has a maximum depth at the center of jaw 6320. In other words, groove 6365 has a maximum depth removed from the edges of jaw 6320.

FIG. 22 shows a cut-away view of groove 6365 in jaw 6320 with projection 6366 in jaw 6620 when needle holder 6000 is in the closed position. The cut-away view of FIG. 22 is taken along the same position at that of the cut-away view of FIG. 21. Needle holder 6000 has three arc-shaped grooves that each mate with a respective one of three projections. The locations of the grooves of needle holder 6000 are the same as the locations of needle holder 4000. The locations of the projections of needle holder 6000 are the same as the locations of the projections of needle holder 4000. Other portions of needle holder 6000 are the same as corresponding portions of needle holder 4000.

The preferred methods for using the needle holders of the second, third, and fourth embodiments of the invention correspond to the preferred method for using the needle holder of the first embodiment of the invention, described above.

Thus, the needle holders of the preferred embodiments of the invention permit efficient surgical maneuvers, while avoiding some of the disadvantages of conventional needle holders. The grooves of the preferred needle holder provide a reference point for the position of the needle within the holder. Thus, once the a needle is loaded within the holder it is less likely the needle will need to be repositioned directly by hand, and the transmission of disease through such a repositioning maneuver is, therefore, avoided.

The grooves of the needle holders of the preferred embodiments of the invention also enhance the stability of the needle within the preferred needle holder, keeping the needle straight to promote uniform sutures. This enhanced stability allows the surgeon to hold the needle closer to the tip of the needle holder, thereby permitting finer control of the needle and allowing better access when suturing is performed in a deep cavity. In contrast, the stability limitations of conventional needle holders may require the surgical team to load the needle further back from the tip of the needle holder than considerations of control and accessibility would indicate.

Although hemostat-type needle holders with ratchet locks have been illustrated, the invention may be practiced with other types of needle holders and locking mechanisms.

Additional advantages and modifications will readily occur to those skilled in the art. The invention in its broader aspects is therefore not limited to the specific details, representative apparatus, and illustrative examples shown and described. Accordingly, departures may be made form such details without departing from the spirit or the scope of applicant's general inventive concept. The invention is defined in the following claims.

What is claimed is:

1. A surgical needle holder comprising:
 a first member including a first handle and a first jaw coupled to the first handle, the first jaw defining a first flat surface; and
 a second member, pivotally coupled to the first member to allow movement of the needle holder between an open position and a closed position, including a second handle and a second jaw coupled to the second handle, the second jaw defining a longitudinal axis, and a plurality of grooves each defining a groove width, each groove oriented transverse to the longitudinal axis, wherein a ratio of a distance between adjacent grooves and a groove width is greater than 5.

2. In an operating theater having a needle, surgical suture coupled to the needle, the surgical needle holder recited in claim 1, and a wound, the wound including subcutaneous tissue, a first tissue part, and a second tissue part, a method of using the surgical needle holder, the method comprising the step of:
 grasping the needle in a selected one of the plurality of grooves using the surgical needle holder,
 and the subsequent steps, performed a plurality of times of:
 subsequently driving the needle through the first and second tissue parts using the surgical needle holder;
 releasing the needle;
 regrasping the needle in the selected one of the plurality of grooves; and
 pulling the needle free of the first skin part.

3. A surgical needle holder comprising:
 a first member including a first handle and a first jaw coupled to the first handle, the first jaw defining a first flat surface; and
 a second member, pivotally coupled to the first member to allow movement of the needle holder between an open position and a closed position, the second member including a second handle and a second jaw coupled to the second handle, the second jaw defining
 a longitudinal axis,
 a second flat surface defining a length along the longitudinal axis, the second flat surface being opposed to the first flat surface when the needle holder is in the closed position,
 a third flat surface defining a length along the longitudinal axis, the third flat surface being opposed to the first flat surface when the needle holder is in the closed position,
 a fourth flat surface defining a length along the longitudinal axis, the fourth flat surface being opposed to the first flat surface when the needle holder is in the closed position, a first groove between the second and third flat surfaces, the first groove being oriented transverse to the longitudinal axis, the groove having a first rim delineating the second flat surface, and a second rim delineating the third flat surface, the length of the third flat surface being greater than the distance between the first and second rims, a second groove between the third and fourth flat surfaces, the second groove being oriented transverse to the longitudinal axis, the second groove having a third rim delineating the third flat surface, and a fourth rim delineating the fourth flat surface, the length of the fourth flat surface being greater than a distance between the third and fourth rims, wherein a ratio of the length of the second flat surface to the distance between the first and second rims is greater than 5.

* * * * *